United States Patent
Tomishige et al.

(10) Patent No.: US 11,040,334 B2
(45) Date of Patent: Jun. 22, 2021

(54) CATALYST FOR REDUCTION REACTION OF 3,4-DIHYDROXYTETRAHYDROFURAN, AND METHOD FOR PRODUCING 3,4-DIHYDROXYTETRAHYDROFURAN REDUCED PRODUCT

(71) Applicant: DAICEL CORPORATION, Osaka (JP)

(72) Inventors: Keiichi Tomishige, Sendai (JP); Yoshinao Nakagawa, Sendai (JP); Masazumi Tamura, Sendai (JP); Yuuichirou Hirai, Himeji (JP); Yasuteru Kajikawa, Himeji (JP); Keisuke Ono, Himeji (JP)

(73) Assignee: DAICEL CORPORATION, Osaka (JP)

(*) Notice: Subject to any disclaimer, the term of this patent is extended or adjusted under 35 U.S.C. 154(b) by 0 days.

(21) Appl. No.: 16/485,379

(22) PCT Filed: Dec. 28, 2017

(86) PCT No.: PCT/JP2017/047157
§ 371 (c)(1),
(2) Date: Aug. 12, 2019

(87) PCT Pub. No.: WO2018/146978
PCT Pub. Date: Aug. 16, 2018

(65) Prior Publication Data
US 2019/0366304 A1   Dec. 5, 2019

(30) Foreign Application Priority Data
Feb. 13, 2017 (JP) .............................. JP2017-023959

(51) Int. Cl.
*B01J 23/68* (2006.01)
*B01J 21/18* (2006.01)
*B01J 23/10* (2006.01)
*B01J 37/02* (2006.01)
*B01J 37/03* (2006.01)
*B01J 37/08* (2006.01)
*C07D 307/20* (2006.01)

(52) U.S. Cl.
CPC .............. *B01J 23/688* (2013.01); *B01J 21/18* (2013.01); *B01J 23/10* (2013.01); *B01J 37/0201* (2013.01); *B01J 37/0236* (2013.01); *B01J 37/035* (2013.01); *B01J 37/08* (2013.01); *C07D 307/20* (2013.01)

(58) Field of Classification Search
CPC ........ B01J 23/688; B01J 37/08; B01J 37/035; B01J 37/0236; B01J 37/0201; B01J 23/10; B01J 21/18; B01J 23/36; C07D 307/20; C07D 307/08; C07C 31/20; C07C 31/12; C07C 29/132; C07C 27/04; C07B 61/00
See application file for complete search history.

(56) References Cited

U.S. PATENT DOCUMENTS

| | | | |
|---|---|---|---|
| 5,969,164 A | 10/1999 | Budge et al. | |
| 2015/0298101 A1* | 10/2015 | Tomishige | ........... B01J 23/6567 549/475 |
| 2019/0262805 A1* | 8/2019 | Tomishige | ............... B01J 29/48 |

FOREIGN PATENT DOCUMENTS

| | | |
|---|---|---|
| CA | 2215544 A1 | 3/1998 |
| JP | 7-82191 A | 3/1995 |
| JP | 10-152450 A | 6/1998 |
| JP | 10-192709 A | 7/1998 |
| WO | WO-2014188843 A1 * | 11/2014 ........... C07D 307/20 |

OTHER PUBLICATIONS

WO-2014188843-A1 2014 WIPO English machine translation p. 1-54.*
International Search Report and Written Opinion of the International Searching Authority (Forms PCT/ISA/210 and PCT/ISA/237) for International Application No. PCT/JP2017/047157, dated Mar. 6, 2018, with English translations.

* cited by examiner

*Primary Examiner* — John M Mauro
(74) *Attorney, Agent, or Firm* — Birch, Stewart, Kolasch & Birch, LLP

(57) ABSTRACT

Provided is a catalyst for reduction reaction with which 1,4-butanediol or tetrahydrofuran can be obtained with higher selectivity than with the related art, using a raw material derived from biomass. The catalyst is used in a reduction reaction of 3,4-dihydroxytetrahydrofuran with hydrogen, wherein the catalyst contains metal catalysts (1) and (2) below; metal catalyst (1): a catalyst containing M1 and M2 below as metal species and supported on a carrier; and metal catalyst (2): a catalyst containing M1 below as a metal species and supported on a carrier; M1: one or more selected from the group consisting of iron and elements belonging to periods 4 to 6 and groups 5 to 7 of the periodic table; and M2: one or more selected from the group consisting of ruthenium, osmium, and elements belonging to periods 4 to 6 and groups 9 to 11 of the periodic table.

16 Claims, 1 Drawing Sheet

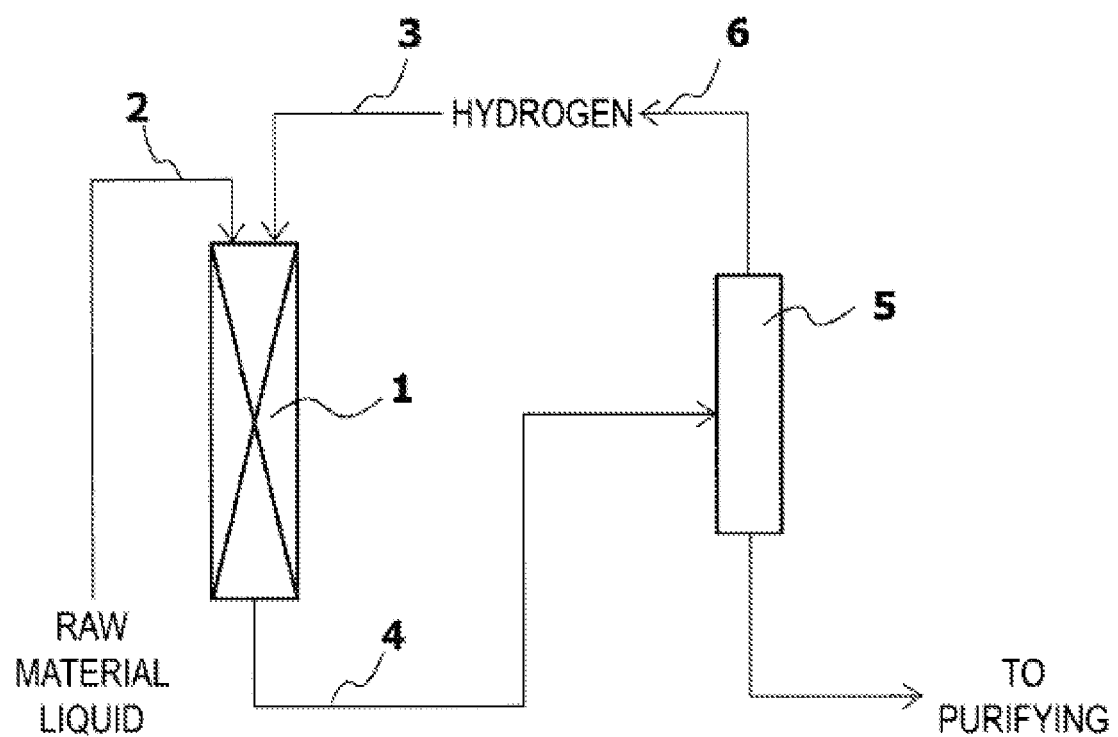

US 11,040,334 B2

CATALYST FOR REDUCTION REACTION OF 3,4-DIHYDROXYTETRAHYDROFURAN, AND METHOD FOR PRODUCING 3,4-DIHYDROXYTETRAHYDROFURAN REDUCED PRODUCT

TECHNICAL FIELD

The present invention relates to a catalyst used in a reduction reaction with hydrogen using 3,4-dihydroxytetrahydrofuran as a raw material, and a method for producing a reduced product using the catalyst.

BACKGROUND ART

Diols, such as 1,4-butanediol, are important compounds used in raw materials for polyester and polyurethane, and the like. In addition, tetrahydrofuran (THF) is an important compound used as a solvent for synthesis reactions and the like.

For example, 1,4-butanediol is known to be produced by a method of using butadiene as a substrate and subjecting it to diacetoxylation at the 1- and 4-positions using a palladium catalyst and acetic acid, followed by reduction and hydrolysis (see, e.g., Patent Documents 1 and 2). In addition, a method of reducing an ester or an anhydride of maleic acid or succinic acid to produce 1,4-butanediol is also known (see, e.g., Patent Document 3).

On the other hand, at present, to produce chemical products, chemical fuel resources, such as mainly petroleum, are consumed in large quantities. That is, in present society, the current status is that carbon is released unilaterally from the ground to the atmosphere. As a result, problems, such as global warming and depletion of fossil fuel resources, have arisen, and for such problems, the creation of a sustainable society, which uses recycled carbon and circulates carbon with the help of photosynthesis of plants, utilizing what is called biomass (e.g., plant-derived resources, such as cellulose, glucose, and vegetable oils) is being sought in recent years.

CITATION LIST

Patent Document

Patent Document 1: JP 07-82191 A
Patent Document 2: JP 10-152450 A
Patent Document 3: JP 10-192709 A

SUMMARY OF INVENTION

Technical Problem

However, chemical fuel resources, such as butadiene, a maleic acid ester, and a succinic acid ester, are used as raw materials in the production of 1,4-butanediol in Patent Documents 1 to 3.

Accordingly, an object of the present invention is to provide a catalyst (catalyst for reduction reaction) with which 1,4-butanediol or tetrahydrofuran can be obtained with higher selectivity than in the related art, using a raw material derived from biomass.

Another object of the present invention is to provide a method capable of producing 1,4-butanediol or tetrahydrofuran with higher selectivity than in the related art, using a raw material derived from biomass.

Solution to Problem

As a result of diligent studies to solve the above problems, the present inventors found that in a reaction using a raw material 3,4-dihydroxytetrahydrofuran that can be produced from a raw material derived from biomass, when a particular catalyst is used to allow 3,4-dihydroxytetrahydrofuran to react with hydrogen, 1,4-butanediol or tetrahydrofuran (they may be herein referred to as a "particular reduced product") is produced with higher selectivity than in the related art. The present invention has been completed based on these findings.

That is, the present invention provides a first catalyst for reduction reaction of 3,4-dihydroxytetrahydrofuran, the catalyst being used in a reaction for reducing 3,4-dihydroxytetrahydrofuran by reaction with hydrogen, wherein the catalyst contains a metal catalyst (1) and a metal catalyst (2) below;

metal catalyst (1): a catalyst containing M1 and M2 below as metal species and supported on a carrier; and metal catalyst (2): a catalyst containing M1 below as a metal species and supported on a carrier;

M1: one or more selected from the group consisting of iron and elements belonging to periods 4 to 6 and belonging to groups 5 to 7 of the periodic table; and M2: one or more selected from the group consisting of ruthenium, osmium, and elements belonging to periods 4 to 6 and belonging to groups 9 to 11 of the periodic table.

In the first catalyst for reduction reaction, the M1 in the metal catalyst (1) is preferably rhenium, and the M2 in the metal catalyst (1) is preferably gold.

In the first catalyst for reduction reaction, the carrier in the metal catalyst (1) is preferably cerium oxide.

In the first catalyst for reduction reaction, the M1 in the metal catalyst (2) is preferably rhenium.

In the first catalyst for reduction reaction, the carrier in the metal catalyst (2) is preferably an activated carbon.

In addition, the present invention provides a first method for producing a 3,4-dihydroxytetrahydrofuran reduced product, the method including reducing 3,4-dihydroxytetrahydrofuran by reaction with hydrogen, wherein the reaction of 3,4-dihydroxytetrahydrofuran and hydrogen in the reducing is allowed to proceed in the presence of the first catalyst for reduction reaction.

In the first production method, preferably, the reaction of 3,4-dihydroxytetrahydrofuran and hydrogen in the reducing is allowed to proceed by performing the reaction in the presence of the metal catalyst (1) in a first stage and performing the reaction in the presence of the metal catalyst (2) in a second stage, or by performing the reaction in the presence of a mixed catalyst of the metal catalyst (1) and the metal catalyst (2).

In the first production method, the reaction of 3,4-dihydroxytetrahydrofuran and hydrogen in the reducing is preferably performed in an atmosphere with a hydrogen partial pressure of 3 MPa or higher.

The first production method preferably includes subjecting erythritol to cyclodehydration to obtain 3,4-dihydroxytetrahydrofuran reduction product prior to the reducing 3,4-dihydroxytetrahydrofuran.

In addition, the present invention provides a second catalyst for reduction reaction of 3,4-dihydroxytetrahydrofuran, the catalyst being used in a reaction for reducing 3,4-dihydroxytetrahydrofuran by reaction with hydrogen, wherein the catalyst contains a catalyst (A) and a catalyst (B) below; and the catalyst (A) and/or the catalyst (B) are catalysts in which M1 below is supported as a metal species;

catalyst (A): an inorganic oxide on which M1 below may be supported as a metal species; and catalyst (B): an activated carbon on which M1 below may be supported as a metal species;

M1: one or more selected from the group consisting of iron and elements belonging to periods 4 to 6 and belonging to groups 5 to 7 of the periodic table.

In the second catalyst for reduction reaction, the M1 is preferably rhenium.

In the second catalyst for reduction reaction, the inorganic oxide in the catalyst (A) is preferably cerium oxide.

In the second catalyst for reduction reaction, preferably, the catalyst (B) is a catalyst in which the M1 is supported as a metal species, and more preferably, the catalyst (A) and the catalyst (B) are catalysts in which the M1 is supported as a metal species.

In addition, the present invention provides a second method for producing a 3,4-dihydroxytetrahydrofuran reduced product, the method including reducing 3,4-dihydroxytetrahydrofuran by reaction with hydrogen, wherein the reaction of 3,4-dihydroxytetrahydrofuran and hydrogen in the reducing is allowed to proceed in the presence of the second catalyst for reduction reaction of 3,4-dihydroxytetrahydrofuran.

In the second production method, preferably, the reaction of 3,4-dihydroxytetrahydrofuran and hydrogen in the reducing is allowed to proceed by performing the reaction in the presence of the catalyst (A) in a first stage and performing the reaction in the presence of the catalyst (B) in a second stage, or by performing the reaction in the presence of a mixed catalyst of the metal catalyst (1) and the metal catalyst (2).

Advantageous Effects of Invention

The catalyst for reduction reaction according to an embodiment of the present invention has the above configuration, and thus 1,4-butanediol or tetrahydrofuran can be obtained with higher selectivity than in the related art, using a raw material derived from biomass. Therefore, in the case where a raw material derived from biomass is used, the load imposed on the environment is small, and such use greatly contributes to the creation of sustainable society. In addition, by using a particular catalyst as the catalyst for reduction reaction according to an embodiment of the present invention, 1,4-butanediol or tetrahydrofuran can be produced with higher selectivity than in the related art.

BRIEF DESCRIPTION OF DRAWINGS

The FIGURE is a flow diagram illustrating an example of reducing in the production method according to an embodiment of the present invention in the case of using a trickle-bed reactor.

DESCRIPTION OF EMBODIMENTS

Catalyst for Reduction Reaction According to Embodiment of Present Invention

The catalyst for reduction reaction according to an embodiment of the present invention is a catalyst used in a reaction to reduce 3,4-dihydroxytetrahydrofuran by reaction with hydrogen (a catalyst for reduction reaction of 3,4-dihydroxytetrahydrofuran). A first catalyst for reduction reaction according to an embodiment of the present invention contains a metal catalyst (1) and a metal catalyst (2). Only one type of metal species may be used each in the metal catalyst (1) and the metal catalyst (2), or two or more types of metal species may be used therein each. In addition, a second catalyst for reduction reaction according to an embodiment of the present invention contains a catalyst (A) and a catalyst (B). Only one type of metal species may be used each in the catalyst (A) and the catalyst (B), or two or more types of metal species may be used therein each. Here, in the present specification, the "first catalyst for reduction reaction according to an embodiment of the present invention" and the "second catalyst for reduction reaction according to an embodiment of the present invention" may be collectively referred to as the "catalyst for reduction reaction according to an embodiment of the present invention".

Metal Catalyst (1)

The metal catalyst (1) is a catalyst containing M1 and M2 as metal species and supported on a carrier. The metal catalyst (1) is a catalyst in which both the M1 and the M2 are supported on one carrier. Note that the M1 in the metal catalyst (1) may be referred to as "M1a". For the M1a, the M2, and the carrier, one type may be used alone, or two or more types may be used in combination.

The M1 (M1a) is one or more selected from the group consisting of iron and elements belonging to periods 4 to 6 and belonging to groups 5 to 7 of the periodic table. Specifically, examples thereof include vanadium (V), chromium (Cr), manganese (Mn), iron (Fe), niobium (Nb), molybdenum (Mo), technetium (Tc), tantalum (Ta), tungsten (W), and rhenium (Re). Among them, vanadium, chromium, manganese, iron, molybdenum, tungsten, and rhenium are preferred, and rhenium is particularly preferred. These metals listed as the M1 generally have a common property of tendency to exhibit high affinity and high reactivity with a compound having a hydroxy group (OH group).

The M2 is one or more selected from the group consisting of ruthenium, osmium, and elements belonging to periods 4 to 6 and belonging to groups 9 to 11 of the periodic table. Specifically, examples thereof include cobalt (Co), nickel (Ni), copper (Cu), ruthenium (Ru), rhodium (Rh), palladium (Pd), silver (Ag), osmium (Os), iridium (Ir), platinum (Pt), and gold (Au). Among them, gold and iridium are preferred. These metals listed as M2 have a common property of being a metal having high affinity to hydrogen and high reduction effect. Among them, gold and iridium (in particular, gold) have a moderate reduction effect to produce 1,4-butanediol, with tendency to produce 1,4-butanediol with high selectivity.

The aspect of the M1a and the M2 contained in the metal catalyst (1) is not particularly limited, but examples thereof include metals, metal salts, metal oxides, metal hydroxides, or an aspect that the metal is contained as a metal complex in a state of being supported on a carrier.

A well-known or commonly used carrier used for a catalyst can be used as the carrier and the carrier is not particularly limited. Examples thereof include an inorganic carrier, such as an inorganic oxide or activated carbon; and an organic carrier, such as an ion exchange resin. Among them, an activated carbon and inorganic oxide are preferred from the viewpoint of the reaction activity.

A well-known or commonly used activated carbon can be used as the activated carbon and the activated carbon is not particularly limited. The activated carbon obtained from any raw material, such as plant-based, mineral-based, and resin-based, can be used. Commercially available products can be also used as the activated carbon, for example, such as those under trade name "Vulcan XC72" (available from CABOT Corporation), trade name "BP2000" (available from CABOT Corporation), trade name "Shirasagi FAC-10"

(available from Japan Envirochemicals, Ltd.), trade name "Shirasagi M" (available from Japan Envirochemicals, Ltd.), trade name "Shirasagi C" (available from Japan Envirochemicals, Ltd.), and trade name "Carboraffin" (available from Japan Envirochemicals, Ltd.).

A well-known or commonly used inorganic oxide can be used as the inorganic oxide and the inorganic oxide is not particularly limited. Examples thereof include cerium oxide ($CeO_2$), titania ($TiO_2$), zirconia ($ZrO_2$), sulphated zirconia, zirconia hydrogen phosphate, magnesium oxide (MgO), zinc oxide (ZnO), silica ($SiO_2$), alumina ($Al_2O_3$), calcium oxide (CaO), molybdenum oxides ($MoO_2$ and $MoO_3$), vanadium oxides (VO and $V_2O_5$), tungsten oxides ($W_2O_3$, $WO_2$, and $WO_3$), tin oxides (SnO, $SnO_2$, and $SnO_3$), rhenium oxides ($ReO_2$, $ReO_3$, and $Re_2O_7$), niobium oxides ($Nb_2O_5$), and a complex of two or more types of these inorganic oxides (e.g., such as zeolites and titanosilicates). Among them, those exhibiting a solid basic property are preferred, and silica, zirconia, sulfated zirconia, zirconia hydrogen phosphate, titania, titanosilicate, alumina, calcium oxide, zinc oxide, molybdenum oxides, vanadium oxides, tungsten oxides, tin oxides, rhenium oxides, niobium oxides, cerium oxide, and magnesium oxide are preferred.

Commercially available products can be also used as the inorganic oxide, for example, such as those under trade name "TIO-4" (titania, available from Nippon Aerosil Co., Ltd.), trade name "500 A" (magnesia, available from Ube Industries, Ltd.), trade name "G-6" (silica, available from Fuji Silicia Chemical, Co., Ltd.), trade name "KHO-24" (alumina, available from Sumitomo Chemical Co., Ltd.), and trade name "Zirconia" (available from Wako Pure Chemical Industries, Ltd.).

Among them, cerium oxide is preferred as the carrier, from the viewpoint of selectivity of a particular reduced product.

Thus, the metal catalyst (1) is preferably a catalyst in which gold and one or more metal species selected from the group consisting of vanadium, chromium, manganese, iron, molybdenum, tungsten, and rhenium (in particular, rhenium) are supported on cerium oxide.

The specific surface area of the carrier is not particularly limited, but is preferably 50 $m^2/g$ or greater (e.g., from 50 to 1500 $m^2/g$, preferably from 100 to 1000 $m^2/g$) in that the metal species are well dispersed, aggregation thereof can be prevented, and the catalytic activity per unit weight can be improved. When the specific surface area of the carrier is within the above range, the catalytic activity per unit weight tends to further improve.

The average particle size of the carrier is not particularly limited, but is preferably from 100 to 10000 μm and more preferably from 1000 to 10000 μm from the viewpoint of reactivity; and absence of excess pressure loss in the case of carrying out the reaction in a continuous flow format. In addition, the shape of the carrier may be any of a powder form, a granular form, a molded form (molded body form), or the like, and is not particularly limited.

The amount of the M1a supported on the carrier is not particularly limited, but is preferably from 0.01 to 50 wt. %, more preferably from 0.05 to 30 wt. %, still more preferably from 0.1 to 10 wt. %, and particularly preferably from 0.15 to 3 wt. %, based on the total amount of the M1a, the M2 and the carrier (100 wt. %). When the M1a is supported in an amount of 0.01 wt. % or greater, the selectivity of a particular reduced product tends to further improve. On the other hand, when the M1a is supported in an amount of 50 wt. % or less, the conversion of 3,4-dihydroxytetrahydrofuran tends to improve, and the yield of the particular reduced product tends to improve. It is presumed that this is because the smaller the amount of the M1a supported within the above range, the smaller the particle size of the M2 supported on the carrier tends to be smaller, and this results in relatively increased catalytic activity, catalyst life, and selectivity of a particular reduced product. Here, the amount of the M1a supported is calculated in terms of metal (e.g., in the case where the M1a is supported as an oxide, the amount of the M1a is calculated in terms of a metal atom constituting the oxide), and in the case of using two or more types of metal species as the M1a, the amount is the total amount thereof.

The ratio (molar ratio) of the M2 to the M1a [M2/M1a] in the metal catalyst (1) is not particularly limited, but is preferably from 0.002 to 50, more preferably from 0.005 to 10, still more preferably from 0.01 to 5, and particularly preferably from 0.02 to 0.7. The amount of the M2 used can be adjusted appropriately within the above range according to temperature, time, and the like for allowing 3,4-dihydroxytetrahydrofuran and hydrogen to react. Here, the numbers of moles of the M1a and the M2 in the above molar ratio is calculated in terms of metal (e.g., in the case where the M1a and the M2 are supported as oxides, the numbers of moles are calculated in terms of a metal atom constituting the oxides), and in the case where two or more types of metal species are used as the M1a and the M2, the amounts are the total amounts thereof. In addition, the ratio of rhenium and gold (molar ratio) [Au/Re] is particularly preferably within the above range.

The method for supporting the M1a and the M2 on the carrier is not particularly limited, and they can be supported on the carrier by a well-known or commonly used method for supporting. Specifically, examples thereof include an impregnation method, a co-precipitation method, and a deposition-precipitation method. Among them, from the viewpoint of improving the conversion of 3,4-dihydroxytetrahydrofuran and improving the yield of a particular reduced product, the method for supporting the M1a is preferably an impregnation method and the method for supporting the M2 is preferably an impregnation method or a deposition-precipitation method.

In the case of supporting the M1a by the impregnation method, the M1a may be supported on the carrier by impregnating a carrier or a carrier on which the M2 is supported with a solution containing the M1a (e.g., an aqueous solution of ammonium perrhenate in the case where the M1a is rhenium); then subjecting to drying and calcining (preferably calcining in air); and further subjecting to reduction with hydrogen or the like as necessary. Here, in the impregnation method, the amount of the M1a supported can be controlled by adjusting the concentration of the solution containing the M1a described above, impregnation into the carrier, and the number of drying treatment and calcination treatment. In addition, in the impregnation method, the temperature for impregnation of the solution containing the M1a, the temperature for drying the carrier impregnated with the solution, and the temperature for calcining the carrier are not particularly limited. Furthermore, the reduction may be performed also in the co-precipitation method or the deposition-precipitation method from the viewpoint of increasing the initial activity of the reaction and possibility of sufficiently exploiting the catalytic performance. After drying the carrier, the temperature for calcining the carrier or the temperature for reducing the carrier is not particularly limited, but, for example, it is preferably from 250 to 550° C. and more preferably from 300 to 500° C., in a hydrogen atmosphere. After the reduction treatment, passivation may be performed as necessary. Performing passivation tends to facilitate handling of the catalyst for reduction reaction according to an embodiment of the present invention. Here, the passivation can be carried out by a well-known or commonly used method and not particularly limited, but, for example, it can be carried out by exposing the carrier to an oxygen atmosphere at a temperature at or near room temperature.

In the case of supporting the M2 by the impregnation method, the M2 may be supported in the same manner as in the impregnation method for supporting the M1a described above. The method includes impregnating a carrier or a carrier on which the M1a is supported with a solution containing the M2 (e.g., an aqueous solution of chloroauric acid in the case where the M2 is gold); subjecting to drying and calcining (preferably calcining in air); and further subjecting to reduction with hydrogen or the like as necessary. More specifically, examples thereof include a method of impregnating the carrier with a solution containing the M2; subjecting to drying and calcining; and then further subjecting to reduction with hydrogen or the like as necessary. Here, the temperature for impregnation of the solution containing the M2, the temperature for drying the carrier impregnated with the solution, the temperature for calcining the carrier, and the temperature for reducing the carrier are not particularly limited. In addition, the reduction treatment after impregnation of the solution containing the M1a described above and the reduction treatment after impregnation of the solution containing the M2 can be carried out simultaneously, for example, by heating in a hydrogen atmosphere after impregnating both solutions (e.g., the heating temperature is preferably from 100 to 700° C. and more preferably from 200 to 600° C.).

In the case of supporting the M2 by the deposition-precipitation method, examples of the method include a method of adjusting the pH of a solution containing the M2 (e.g., an aqueous solution of chloroauric acid in the case where the M2 is gold) with an alkaline aqueous solution as necessary (e.g., adjusting the pH to 6 to 10), adding therein the carrier or a carrier on which the M1a is supported; after a lapse of a predetermined time, washing with water; subjecting to drying and calcining (preferably calcining in air); and then further subjecting to reduction with hydrogen or the like as necessary. Here, the temperature for adjusting the pH with an alkaline aqueous solution, the temperature for drying the carrier, the temperature for calcining the carrier, and the temperature for reducing the carrier are not particularly limited.

Preferred methods for preparing the metal catalyst (1) include preferably (i) a method of supporting the M1a and the M2 one after another on a carrier each by the impregnation method; (ii) a method of supporting the M2 on a carrier by the deposition-precipitation method and then supporting the M1a by the impregnation method; (iii) a method of supporting the M1a on a carrier by the impregnation method and then supporting the M2 by the deposition-precipitation method; and (iv) a method of preparing a carrier supporting the M2 by the co-precipitation method, and supporting the M1a thereon by the impregnation method. Here, in the above (i), supporting by the impregnation method may be in the order of supporting the M1a first or supporting the M2 first.

The average particle size of the metal catalyst (1) is not particularly limited, but is preferably from 100 to 10000 µm and more preferably from 1000 to 10000 µm from the viewpoint of reactivity; and absence of excess pressure loss in the case of carrying out the reaction in a continuous flow format. In addition, the shape of the metal catalyst (1) is not particularly limited, but examples thereof include a powder form, a granular form, and a molded form (molded body form).

Metal Catalyst (2)

The metal catalyst (2) is a catalyst containing the M1 as a metal species and supported on a carrier. Here, the carrier in the metal catalyst (2) does not support the M2. In addition, the M1 in the metal catalyst (2) may be the same metal species as the M1 in the metal catalyst (1), or may be a different metal species. The M1 in the metal catalyst (2) may be referred to as "M1b". For the M1b and the carrier, one type may be used alone, or two or more types may be used in combination.

The M1 (M1b) is one or more selected from the group consisting of iron and elements belonging to periods 4 to 6 and belonging to groups 5 to 7 of the periodic table; and examples thereof include the same as those exemplified for the M1a in the metal catalyst (1) described above. Among them, vanadium, chromium, manganese, iron, molybdenum, tungsten, and rhenium are preferred, as the M1b in the metal catalyst (2). In particular, rhenium is preferred from the viewpoint of obtaining a particular reduced product with high selectivity and high yield.

The aspect of the M1b contained in the metal catalyst (2) is not particularly limited, but examples thereof include metals, metal salts, metal oxides, metal hydroxides, or an aspect that the metal is contained as a metal complex in a state of being supported on a carrier.

A well-known or commonly used carriers used for catalysts can be used as the carrier, and examples thereof include the same carriers as those in the metal catalyst (1) described above. Among them, preferred carriers in the metal catalyst (2) include silica, zirconia, sulfated zirconia, zirconia hydrogen phosphate, titania, titanosilicate, alumina, calcium oxide, zinc oxide, molybdenum oxides, vanadium oxides, tungsten oxides, tin oxides, rhenium oxides, niobium oxides, cerium oxide, and magnesium oxide. In particular, in the case where 1,4-butanediol is desired to be obtained as a reduced product with high selectivity and high yield, an activated carbon is preferred, and in the case where tetrahydrofuran is desired to be obtained with high selectivity, an inorganic oxide is preferred. Furthermore, in the case where tetrahydrofuran is desired to be obtained with high selectivity and high yield, an inorganic oxide other than inorganic oxides containing silica (such as silica, zeolites, and titanosilicates) is preferred.

Thus, in the case where 1,4-butanediol is desired to be obtained with high selectivity and high yield, the metal catalyst (2) is preferably a catalyst in which one or more metal species selected from the group consisting of vanadium, chromium, manganese, iron, molybdenum, tungsten, and rhenium (in particular, rhenium) are supported on an activated carbon. Furthermore, in the case where tetrahydrofuran is desired to be obtained with high selectivity, the metal catalyst (2) is preferably a catalyst in which one or more metal species selected from the group consisting of vanadium, chromium, manganese, iron, molybdenum, tungsten, and rhenium (in particular, rhenium) are supported on an inorganic oxide (in particular, in the case where tetrahydrofuran is desired to be obtained with high selectivity and high yield, an inorganic oxide other than inorganic oxides containing silica (such as silica, zeolites, and titanosilicates)).

The specific surface area of the carrier is not particularly limited, but is preferably 50 m$^2$/g or greater (e.g., from 50 to 1500 m$^2$/g, preferably from 100 to 1000 m$^2$/g) in that the metal species are well dispersed, aggregation thereof can be prevented, and the catalytic activity per unit weight can be improved. When the specific surface area of the carrier is within the above range, the catalytic activity per unit weight tends to further improve.

The average particle size of the carrier is not particularly limited, but is preferably from 100 to 10000 μm and more preferably from 1000 to 10000 μm from the viewpoint of reactivity; and absence of excess pressure loss in the case of carrying out the reaction in a continuous flow format. In addition, the shape of the carrier may be any of a powder form, a granular form, a molded form (molded body form), or the like, and is not particularly limited.

The amount of the M1b supported on the carrier is not particularly limited, but is preferably from 0.01 to 60 wt. %, more preferably from 0.05 to 50 wt. %, and still more preferably from 0.1 to 20 wt. %, based on the total amount of the M1b and the carrier (100 wt. %). When the M1b is supported in an amount of 0.01 wt. % or greater, the selectivity of a particular reduced product tends to further improve. On the other hand, when the M1b is supported in an amount of 60 wt. % or less, the conversion of 3,4-dihydroxytetrahydrofuran tends to improve, and the yield of a particular reduced product tends to improve. Here, the amount of the M1b supported is calculated in terms of metal (e.g., in the case where the M1b is supported as an oxide, calculated in terms of a metal atom constituting the oxide), and in the case where two or more types of metal species are used as the M1b, the amount is the total amount thereof.

The method for supporting the M1b on the carrier is not particularly limited, and it can be supported on the carrier by a well-known or commonly used method for supporting. Specifically, examples thereof include an impregnation method, a co-precipitation method, and a deposition-precipitation method. Among them, an impregnation method is preferred from the viewpoint of improving the conversion of 3,4-dihydroxytetrahydrofuran and improving the yield of a particular reduced product. Here, the preferred conditions for supporting the M1b on the carrier by the impregnation method are the same as those for the impregnation method for the M1a in the metal catalyst (1) described above.

The average particle size of the metal catalyst (2) is not particularly limited, but is preferably from 100 to 10000 μm and more preferably from 1000 to 10000 μm from the viewpoint of reactivity; and absence of excess pressure loss in the case of carrying out the reaction in a continuous flow format. In addition, the shape of the metal catalyst (2) is not particularly limited, but examples thereof include a powder form, a granular form, and a molded form (molded body form).

A first catalyst for reduction reaction according to an embodiment of the present invention contains a metal catalyst (1) and a metal catalyst (2). The content ratio (weight ratio) of the metal catalyst (1) and the metal catalyst (2) [metal catalyst (1)/metal catalyst (2)] is not particularly limited, but is preferably from 0.03 to 10, more preferably from 0.07 to 5, and still more preferably from 0.1 to 2 from the viewpoint of improving the conversion of 3,4-dihydroxytetrahydrofuran and the selectivity of a particular reduced product. Here, the ratio of the metal catalyst (1) and the metal catalyst (2) used in a first production method according to an embodiment of the present invention described later is also preferably within the above range.

In the case where only the metal catalyst (1) is used as the catalyst for allowing 3,4-dihydroxytetrahydrofuran and hydrogen to react without using the metal catalyst (2), the selectivity of 1,4-butanediol or tetrahydrofuran is approximately a few %. In addition, in the case where only the metal catalyst (2) is used without using the metal catalyst (1), the selectivity of 1,4-butanediol or tetrahydrofuran is not so high, and the conversion of 3,4-dihydroxytetrahydrofuran is also as extremely low as a few %. On the other hand, in the case where the first catalyst for reduction reaction according to an embodiment of the present invention is used, 1,4-butanediol or tetrahydrofuran can be obtained with higher selectivity than in the related art.

Catalyst (A) and Catalyst (B)

A second catalyst for reduction reaction according to an embodiment of the present invention contains a catalyst (A) and a catalyst (B). The catalyst (A) and/or the catalyst (B) are catalysts in which the M1 is supported as a metal species. That is, at least one of the catalyst (A) or the catalyst (B) is a catalyst in which the M1 is supported as a metal species. In particular, from the viewpoint of improving the conversion of 3,4-dihydroxytetrahydrofuran and the selectivity of 1,4-butanediol, preferably at least the catalyst (B) is a catalyst in which the M1 is supported as a metal species, and more preferably, both the catalyst (A) and the catalyst (B) are a catalyst in which the M1 is supported as a metal species.

The catalyst (A) is an inorganic oxide on which the M1 may be supported as a metal species. One type each of the M1 and inorganic oxides that may be contained in the catalyst (A) may be used alone, or two or more types each thereof may be used in combination.

Examples of the inorganic oxide include inorganic oxides exemplified as the carrier described above. Among them, inorganic oxides exhibiting a solid basic property are preferred, and silica, zirconia, sulfated zirconia, zirconia hydrogen phosphate, titania, titanosilicate, alumina, calcium oxide, zinc oxide, molybdenum oxides, vanadium oxides, tungsten oxides, tin oxides, rhenium oxides, niobium oxides, cerium oxide, and magnesium oxide are preferred, and from the viewpoint of the selectivity of a particular reduced product, cerium oxide is particularly preferred.

The catalyst (B) is an activated carbon on which the M1 may be supported as a metal species. The M1 in the catalyst (B) may be the same metal species as the M1 in the catalyst (A), or may be a different metal species. For the M1 and the activated carbon that may be contained in the catalyst (B), one type may be used alone, or two or more types may be used in combination.

The M1 that may be contained in the catalyst (A) and/or the catalyst (B) is preferably vanadium, chromium, manganese, iron, molybdenum, tungsten, and rhenium, and particularly preferably rhenium.

The catalyst (A) or the catalyst (B) (i.e., either one of the catalyst (A) or the catalyst (B)) may support the M2 as a metal species. For the M2 that may be contained in the catalyst (A) or the catalyst (B), one type may be used alone, or two or more types may be used in combination. The M2 that may be contained in the catalyst (A) or the catalyst (B) is preferably gold and iridium (in particular, gold), which have a moderate reduction effect to provide 1,4-butanediol, and tend to provide 1,4-butanediol with high selectivity.

In the case where the catalyst (A) and/or the catalyst (B) contain the M1 and/or the M2, the activated carbon and/or the inorganic oxide act as a carrier. The aspect of the M1 and the M2 that may be contained in the catalyst (A) and/or the catalyst (B) is not particularly limited. Examples thereof include metals, metal salts, metal oxides, metal hydroxides, or an aspect that the metal is contained as a metal complex in a state of being supported on a carrier.

The catalyst (A) is preferably cerium oxide; a catalyst in which one or more metal species selected from the group consisting of vanadium, chromium, manganese, iron, molybdenum, tungsten, and rhenium (in particular, rhenium) are supported on cerium oxide; or a catalyst in which gold and one or more metal species selected from the group consisting of vanadium, chromium, manganese, iron, molybdenum, tungsten, and rhenium (in particular, rhenium) are supported on cerium oxide.

Catalyst (B) is preferably an activated carbon; a catalyst in which one or more metal species selected from the group consisting of vanadium, chromium, manganese, iron, molybdenum, tungsten, and rhenium (in particular, rhenium) are supported on an activated carbon; or a catalyst in which gold and one or more metal species selected from the group consisting of vanadium, chromium, manganese, iron, molybdenum, tungsten, and rhenium (in particular, rhenium) are supported on an activated carbon.

The specific surface areas of the inorganic oxide and the activated carbon are not particularly limited, but are preferably 50 $m^2/g$ or greater (e.g., from 50 to 1500 $m^2/g$ and preferably from 100 to 1000 $m^2/g$) from the viewpoint of improving the catalytic activity per unit weight and improving the addition rate. When the specific surface areas of the inorganic oxide and the activated carbon are within the above range, the catalytic activity per unit weight tends to further improve.

The average particle sizes of the inorganic oxide and the activated carbon are not particularly limited, but are preferably from 100 to 10000 μm and more preferably from 1000 to 10000 μm from the viewpoint of reactivity; and absence of excess pressure loss in the case of carrying out the reaction in a continuous flow format. In addition, the shape of the inorganic oxide and the activated carbon may be any of a powder form, a granular form, a molded form (molded body form), or the like, and is not particularly limited.

The amount of the M1 supported on the carrier in the case where the catalyst (A) and/or the catalyst (B) support the M1 and do not support the M2 is not particularly limited, but is preferably from 0.01 to 60 wt. %, more preferably from 0.05 to 50 wt. %, and still more preferably from 0.1 to 20 wt. %, based on the total amount of the M1 and the carrier (100 wt. %). When the M1 is supported in an amount of 0.01 wt. % or greater, the selectivity of a particular reduced product tends to further improve. On the other hand, when the M1 is supported in an amount of 60 wt. % or less, the conversion of 3,4-dihydroxytetrahydrofuran tends to improve, and the yield of a particular reduced product tends to improve. Here, the amount of the M1 supported is calculated in terms of metal (e.g., in the case where the M1 is supported as an oxide, calculated in terms of a metal atom constituting the oxide), and in the case where two or more types of metal species are used as the M1, the amount is the total amount thereof.

The amount of the M1 supported on the carrier in the case where the catalyst (A) or the catalyst (B) supports the M1 and the M2 is not particularly limited, but is preferably from 0.01 to 50 wt. %, more preferably from 0.05 to 30 wt. %, still more preferably from 0.1 to 10 wt. %, and particularly preferably from 0.15 to 3 wt. %, based on the total amount of the M1, the M2, and the carrier (100 wt. %). When the M1 is supported in an amount of 0.01 wt. % or greater, the selectivity of a particular reduced product tends to further improve. On the other hand, when the M1 is supported in an amount of 50 wt. % or less, the conversion of 3,4-dihydroxytetrahydrofuran tends to improve, and the yield of a particular reduced product tends to improve. It is presumed that this is because the smaller the amount of the M1 supported within the above range, the smaller the particle size of the M2 supported on the carrier tends to be, and this results in relatively increased catalytic activity, catalyst life, and selectivity of a particular reduced product. Here, the amount of the M1 supported is calculated in terms of metal (e.g., in the case where the M1 is supported as an oxide, calculated in terms of a metal atom constituting the oxide), and in the case where two or more types of metal species are used as the M1, the amount is the total amount thereof.

The ratio (molar ratio) of the M2 to the M1 [M2/M1] in the case where the catalyst (A) or the catalyst (B) supports the M1 and the M2 is not particularly limited, but is preferably from 0.002 to 50, more preferably from 0.005 to 10, still more preferably from 0.01 to 5, and particularly preferably from 0.02 to 0.7. The amount of the M2 used can be adjusted appropriately within the above range according to temperature, time, and the like for allowing 3,4-dihydroxytetrahydrofuran and hydrogen to react. Here, the number of moles of the M1 and the M2 in the above molar ratio is calculated in terms of metal (e.g., in the case where the M1 and the M2 are supported as oxides, calculated in terms of a metal atom constituting the oxides), and in the case where two or more types of metal species are used as the M1 and the M2, the amount is the total amount thereof. In addition, the ratio of rhenium and gold (molar ratio) [Au/Re] is particularly preferably within the above range.

The method for supporting the M1 and the M2 on the inorganic oxide and/or the activated carbon is not particularly limited, and they can be supported on the carrier by a well-known or commonly used method for supporting. Examples thereof include the method described in the metal catalyst (1) above. In addition, the method for supporting the M1 on the inorganic oxide and/or the activated carbon is not particularly limited, and the M1 can be supported on the carrier by a well-known or commonly used method for supporting. Examples of the method include the method described in the metal catalyst (2) above. In either case, the preferred method for supporting is similar to the method described in the metal catalyst (1) and the metal catalyst (2) above.

The second catalyst for reduction reaction according to an embodiment of the present invention contains the catalyst (A) and the catalyst (B). The content ratio (weight ratio) of the catalyst (A) and the catalyst (B) [catalyst (A)/catalyst (B)] is not particularly limited. The content ratio is preferably from 0.03 to 10, more preferably from 0.07 to 5, and still more preferably from 0.1 to 2 from the viewpoint of improving the conversion of 3,4-dihydroxytetrahydrofuran and the selectivity of 1,4-butanediol. Here, the ratio of the catalyst (A) and the catalyst (B) used in a second production method according to an embodiment of the present invention described later is also preferably within the above range.

In the case where only the catalyst (A) is used as the catalyst for allowing 3,4-dihydroxytetrahydrofuran and hydrogen to react without using the catalyst (B), the selectivity of 1,4-butanediol or tetrahydrofuran is approximately a few %. In addition, in the case where only the metal catalyst (B) is used without using the catalyst (A), the selectivity of 1,4-butanediol or tetrahydrofuran is not so high, and the conversion of 3,4-dihydroxytetrahydrofuran is also as extremely low as a few %. On the other hand, in the case where the second catalyst for reduction reaction according to an embodiment of the present invention is used, 1,4-butanediol or tetrahydrofuran can be obtained with higher selectivity than in the related.

Here, the metal catalyst (1), and the catalyst (A) and the catalyst (B) may overlap each other. Also, the metal catalyst (2), and the catalyst (A) and the catalyst (B) may overlap each other. For example, a catalyst (ReOx-Au/CeO$_2$) may be used as both the metal catalyst (1) and the catalyst (A). Furthermore, a catalyst (ReOx/C) may be used as both the metal catalyst (2) and the catalyst (B). Still more, a catalyst (ReOx/TiO$_2$) may be used as both the metal catalyst (2) and the catalyst (A).

A reduced product of 3,4-dihydroxytetrahydrofuran can be produced by reaction with hydrogen using the catalyst for reduction reaction according to an embodiment of the present invention. Here, a method for producing a 3,4-dihydroxytetrahydrofuran reduced product using the first catalyst for reduction reaction according to an embodiment of the present invention may be referred to as a "first production method according to an embodiment of the present invention", and a method for producing a 3,4-dihydroxytetrahydrofuran reduced product using the second catalyst for reduction reaction according to an embodiment of the present invention may be referred to as a "second production method according to an embodiment of the present invention". In addition, the "first production method according to an embodiment of the present invention" and the "second production method according to an embodiment of the present invention" may be collectively referred to as a "production method according to an embodiment of the present invention". 3,4-dihydroxytetrahydrofuran The above 3,4-dihydroxytetrahydrofuran is a compound represented by Formula (1) below. As indicated in Formula (1), 3,4-dihydroxytetrahydrofuran is a compound having a structure formed by dehydration condensation of hydroxy groups at positions 1 and 4 of erythritol. As 3,4-dihydroxytetrahydrofuran, 1,4-anhydroerythritol (3,4-dihydroxyoxolane) and 1,4-anhydrothreitol are present.

[Chemical Formula 1]

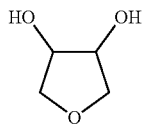

(1)

The above 3,4-dihydroxytetrahydrofuran may be, for example, 3,4-dihydroxytetrahydrofuran produced by chemical synthesis or may be 3,4-dihydroxytetrahydrofuran derived from saccharides, such as glucose, by fermentation technology, and is not particularly limited. Examples of 3,4-dihydroxytetrahydrofuran derived from the fermentation technology include 3,4-dihydroxytetrahydrofuran produced by intramolecular dehydration reaction of erythritol used as a raw material, the erythritol derived from saccharides, such as glucose, by fermentation technology. The intramolecular dehydration reaction can be carried out by a well-known or commonly used method and is not particularly limited. Here, 3,4-dihydroxytetrahydrofuran (unreacted 3,4-dihydroxytetrahydrofuran) recovered from a reaction mixture resulting from reducing described later can be reused as the above 3,4-dihydroxytetrahydrofuran.

Reduced Product

Reaction of 3,4-dihydroxytetrahydrofuran and hydrogen can usually produce a variety of compounds, such as 2,5-dihydrofuran, 2,3-dihydrofuran, tetrahydrofuran, 3-hydroxytetrahydrofuran, 1,4-butanediol, 1,3-butanediol, 1,2-butanediol, 2,3-butanediol, 1-butanol, 2-butanol, and γ-butyrolactone. However, according to a reaction of 3,4-dihydroxytetrahydrofuran and hydrogen using the catalyst for reduction reaction according to an embodiment of the present invention, a particular reduced product can be obtained with high selectivity. For example, in the case where a catalyst in which one or more metal species selected from the group consisting of vanadium, chromium, manganese, iron, molybdenum, tungsten, and rhenium (in particular, rhenium) are supported as the metal catalyst (2) or the catalyst (B) on an activated carbon is used, the conversion of 3,4-dihydroxytetrahydrofuran is high (e.g., 95% or higher) and 1,4-butanediol is produced with high selectivity (e.g., 77% or higher). In addition, in the case where a catalyst in which one or more metal species selected from the group consisting of vanadium, chromium, manganese, iron, molybdenum, tungsten, and rhenium (in particular, rhenium) are supported as the metal catalyst (2) or the catalyst (A) on an inorganic oxide is used, tetrahydrofuran is produced with high selectivity.

Hydrogen

The hydrogen (hydrogen gas) can be used in a state of being substantially alone, or can be used in a diluted state with an inert gas, such as nitrogen, argon, and helium. Furthermore, hydrogen (unreacted hydrogen) recovered from a reaction mixture resulting from reducing described later can be reused.

Method for Producing 3,4-dihydroxytetrahydrofuran Reduced Product

A 3,4-dihydroxytetrahydrofuran reduction product can be produced by performing a method including reducing 3,4-dihydroxytetrahydrofuran by reaction with hydrogen, wherein the reaction of 3,4-dihydroxytetrahydrofuran and hydrogen in the reducing is allowed to proceed in the presence of the catalyst for reduction reaction according to an embodiment of the present invention. Here, in the present specification, the method for producing the 3,4-dihydroxytetrahydrofuran reduced product may be referred to as the "production method according to an embodiment of the present invention". In addition, the "reducing 3,4-dihydroxytetrahydrofuran by reaction with hydrogen" may be referred to as the "reducing".

In the reducing, the reaction of 3,4-dihydroxytetrahydrofuran and hydrogen may be a reaction of a gas-solid two-phase system that allows gaseous (vaporized) 3,4-dihydroxytetrahydrofuran and hydrogen to react in the presence of the catalyst (solid) for reduction reaction according to an embodiment of the present invention, and may be a reaction of a gas-liquid-solid three-phase system that allows liquid 3,4-dihydroxytetrahydrofuran and hydrogen to react in the presence of the catalyst (solid) for reduction reaction according to an embodiment of the present invention. In particular, the reaction is preferably allowed to proceed in the gas-liquid-solid three-phase system from the viewpoint of preventing the formation of compounds having a small number of carbons (for example, 3 or less) resulting from a cleavage of a carbon-carbon bond.

More specifically, the reaction of 3,4-dihydroxytetrahydrofuran and hydrogen in the reducing can be allowed to proceed, for example, by sealing a raw material liquid containing 3,4-dihydroxytetrahydrofuran as an essential component and hydrogen in a reactor and heating in the presence of the catalyst for reduction reaction according to an embodiment of the present invention. In the reducing, the reaction of 3,4-dihydroxytetrahydrofuran and hydrogen may be allowed to proceed by performing the reaction in the presence of the metal catalyst (1) in a first stage and performing the reaction in the presence of the metal catalyst (2) in a second stage, or by performing the reaction in the presence of a mixed catalyst of the metal catalyst (1) and the metal catalyst (2). In the former case, it is presumed that 3,4-dihydroxytetrahydrofuran and hydrogen react to form dihydrofuran (2,3-dihydrofuran and 3,4-dihydrofuran) in the first stage, and dihydrofuran and hydrogen react to form 1,4-butanediol in the second stage, but each elementary reaction in the first and second stages can be performed with higher yield, and 1,4-butanediol can be produced industrially with higher selectivity than performed with a single catalyst. In addition, in the latter case, 1,4-butanediol can be produced in one stage with high conversion and high selectivity. Furthermore, the reaction may be allowed to proceed by performing the reaction in the presence of the catalyst (A) in the first stage and performing the reaction in the presence of the catalyst (B) in the second stage, or by performing the reaction in the presence of a mixed catalyst of the catalyst (A) and the catalyst (B). Here, for the catalyst for reduction reaction according to an embodiment of the present invention, one type can be used alone, or two or more types can be used in combination in the reducing.

In addition to 3,4-dihydroxytetrahydrofuran, the raw material liquid may contain, for example, a solvent, such as water or an organic solvent, or may be substantially free of a solvent. The organic solvent is not particularly limited, and examples thereof include alcohols, such as methanol, ethanol, isopropanol, n-butanol, and 2-butanol; dimethyl sulfoxide (DMSO); dimethylformamide (DMF); dimethylacetamide (DMAc); and 1,4-dioxane. Among them, 1,4-dioxane is preferred from the viewpoint of excellent reactivity of 3,4-dihydroxytetrahydrofuran and hydrogen. Here, one type of the solvent can be used alone, or two or more types thereof can be used in combination.

The concentration of 3,4-dihydroxytetrahydrofuran in the raw material liquid (content of 3,4-dihydroxytetrahydrofuran per 100 wt. % of the raw material liquid) is not particularly limited, but is preferably 5 wt. % or higher (e.g., from 5 to 100 wt. %), more preferably 8 wt. % or higher (e.g., from 8 to 90 wt. % and from 8 to 70 wt. %), and still more preferably 10 wt. % or higher (e.g., from 10 to 60 wt. %). When the concentration is 5 wt. % or higher, the reaction rate (conversion) of 3,4-dihydroxytetrahydrofuran tends to improve. On the other hand, when the concentration is 90 wt. % or less, the viscosity is not too high, tending to facilitate the operation.

The amount (content) of the metal catalyst (1) used in the first catalyst for reduction reaction according to an embodiment of the present invention is not particularly limited, but is preferably from 0.1 to 300 parts by weight, more preferably from 1 to 200 parts by weight, and still more preferably from 5 to 150 parts by weight, per 100 parts by weight of 3,4-dihydroxytetrahydrofuran. When the amount used is within the above range, the effect by using the catalyst is more sufficiently achieved, and the conversion of 3,4-dihydroxytetrahydrofuran and the selectivity of a particular reduced product (in particular, 1,4-butanediol) tend to further improve.

The amount (content) of the metal catalyst (2) used in the first catalyst for reduction reaction according to an embodiment of the present invention is not particularly limited, but is preferably from 0.1 to 300 parts by weight, more preferably from 1 to 200 parts by weight, and still more preferably from 5 to 150 parts by weight, per 100 parts by weight of 3,4-dihydroxytetrahydrofuran. When the amount used is within the above range, the effect by using the catalyst is more sufficiently achieved, and the conversion of 3,4-dihydroxytetrahydrofuran and the selectivity of a particular reduced product (in particular, 1,4-butanediol) tend to further improve.

The amount (content) of the catalyst (A) used in the second catalyst for reduction reaction according to an embodiment of the present invention is not particularly limited, but is preferably from 0.1 to 300 parts by weight, more preferably from 1 to 200 parts by weight, and still more preferably from 5 to 150 parts by weight, per 100 parts by weight of 3,4-dihydroxytetrahydrofuran. When the amount used is within the above range, the effect by using the catalyst is more sufficiently achieved, and the conversion of 3,4-dihydroxytetrahydrofuran and the selectivity of a particular reduced product (in particular, 1,4-butanediol) tend to further improve.

The amount (content) of the catalyst (B) used in the second catalyst for reduction reaction according to an embodiment of the present invention is not particularly limited, but is preferably from 0.1 to 300 parts by weight, more preferably from 1 to 200 parts by weight, and still more preferably from 5 to 150 parts by weight, per 100 parts by weight of 3,4-dihydroxytetrahydrofuran. When the amount used is within the above range, the effect by using the catalyst is more sufficiently achieved, and the conversion of 3,4-dihydroxytetrahydrofuran and the selectivity of a particular reduced product (in particular, 1,4-butanediol) tend to further improve.

It is preferred to include removing the catalyst, such as by filtration, after completion of the reaction.

The reaction of 3,4-dihydroxytetrahydrofuran and hydrogen may be allowed to proceed in the coexistence of a solid acid. That is, the raw material liquid may contain a solid acid in addition to 3,4-dihydroxytetrahydrofuran and the solvent described above. Here, the solid acid is a solid exhibiting properties of Bronsted acid and/or Lewis acid (either or both of Bronsted acid and Lewis acid) and having Hammett acidity function ($H_0$) of 6.8 or less. A well-known or commonly used solid acid can be used as the solid acid, and the solid acid is not particularly limited. Examples thereof include solids in which inorganic acids or organic acids (e.g., such as organic sulfonic acids) are supported on a carrier (such as silica, alumina, zeolites, and silica-alumina); crystalline metal silicates, such as gallium silicate, aluminosilicate, and borosilicate (e.g., such as a proton type zeolite H-ZSM-5); heteropolyacids or salts thereof; solids in which a heteropolyacid or a salt thereof is supported on a carrier (e.g., such as silica and alumina); acidic metal oxides, such as zirconium oxide ($ZrO_2$) and titanium oxide ($TiO_2$); and polymers having acid groups, such as carboxyl groups and sulfonic acid groups (e.g., such as cation exchange resins). Commercially available products can also be used as the solid acid. The reaction of the 3,4-dihydroxytetrahydrofuran and hydrogen described above can be promoted by allowing the reaction to proceed in the coexistence of the solid acid. Here, for the solid acid, one type can be used alone, or two or more types can be used in combination.

In the case where the solid acid is used in the reducing, the amount (content) of the solid acid used is not particularly limited, but is preferably from 0.1 to 50 parts by weight and more preferably from 1 to 20 parts by weight, per 100 parts by weight of 3,4-dihydroxytetrahydrofuran. In the case of allowing the solid acid to coexist, it is preferred to include removing the solid acid by filtration or the like, after completion of the reaction.

An additional component may be allowed to coexist in the reaction within a range not inhibiting the effect according to an embodiment of the present invention. That is, the raw material liquid may contain an additional component (e.g., such as alcohols) within a range not inhibiting the effect according to an embodiment of the present invention. In addition, the raw material liquid may contain an impurity derived from raw materials of 3,4-dihydroxytetrahydrofuran (such as 3,4-dihydroxytetrahydrofuran and raw materials thereof). Such an impurity can degrade the catalyst, and thus it may be preferably removed from the raw material liquid by a well-known or commonly used method (e.g., such as distillation, adsorption, ion exchange, crystallization, and extraction).

The raw material liquid is not particularly limited, but is obtained by mixing 3,4-dihydroxytetrahydrofuran and, as necessary, a solvent, a solid acid, and an additional component. A well-known or commonly used stirrer or the like can be used for mixing.

The molar ratio of hydrogen and 3,4-dihydroxytetrahydrofuran [hydrogen (mol)/3,4-dihydroxytetrahydrofuran (mol)] subjected to the reaction (the reaction of 3,4-dihydroxytetrahydrofuran and hydrogen) is not particularly limited, but is preferably from 1 to 100, more preferably from 1 to 50, and still more preferably from 1 to 30. When the molar ratio is 1 or greater, the reaction rate (conversion) of 3,4-dihydroxytetrahydrofuran tends to improve. On the other hand, when the molar ratio is 100 or less, the utility cost for recovering unreacted hydrogen tends to decrease.

The reaction temperature of 3,4-dihydroxytetrahydrofuran and hydrogen in the reaction is not particularly limited, but is preferably from 50 to 250° C., more preferably from 60 to 220° C., and still more preferably from 70 to 200° C. When the reaction temperature is 50° C. or higher, the reaction rate (conversion) of 3,4-dihydroxytetrahydrofuran tends to improve. On the other hand, when the reaction temperature is 250° C. or lower, 3,4-dihydroxytetrahydrofuran is less likely to be decomposed, and the yield of a particular reduced product tends to improve. Here, the reaction temperature may be controlled to be constant (substantially constant) in the reaction or may be controlled to change stepwise or continuously.

The reaction time of 3,4-dihydroxytetrahydrofuran and hydrogen in the reaction is not particularly limited, but is preferably from 0.1 to 200 hours, more preferably from 0.2 to 150 hours, and still more preferably from 0.5 to 100 hours. When the reaction time is 0.1 hours or longer, the reaction rate (conversion) of 3,4-dihydroxytetrahydrofuran tends to improve. On the other hand, when the reaction time is 200 hours or shorter, the selectivity of a particular reduced product tends to improve.

The reaction pressure of 3,4-dihydroxytetrahydrofuran and hydrogen (hydrogen partial pressure in the reaction of 3,4-dihydroxytetrahydrofuran and hydrogen) in the reaction is not particularly limited, but is preferably 0.1 MPa or higher (e.g., from 0.1 to 50 MPa), more preferably 1 MPa or higher (e.g., from 1 to 30 MPa), still more preferably from 3 MPa or higher (e.g., from 3 to 20 MPa), and even more preferably from 5 MPa or higher (e.g., from 5 to 15 MPa). When the reaction pressure is 0.1 MPa or higher (in particular, 5 MPa or higher), the reaction rate (conversion) of 3,4-dihydroxytetrahydrofuran tends to improve. On the other hand, when the reaction pressure exceeds 50 MPa, the reactor needs to have a high degree of pressure resistance, and thus this tends to increase the production cost.

The reaction can be carried out in any format, such as a batch format, a semi-batch format, and a continuous flow format. In addition, when the amount of a reduced product obtained from a predetermined amount of 3,4-dihydroxytetrahydrofuran is desired to be increased, a process of separating and recovering unreacted 3,4-dihydroxytetrahydrofuran after completion of the reaction may be employed. Employment of this recycling process can increase the amount of a particular reduced product produced when a predetermined amount of 3,4-dihydroxytetrahydrofuran is used.

In the reducing, a well-known or commonly used reactor can be used as the reactor, and, for example, a batch reactor, a fluidized-bed reactor, and a fixed-bed reactor can be used. As the fixed-bed reactor, for example, a trickle-bed reactor can be used. The trickle-bed reactor is a reactor (fixed-bed continuous reactor) in a configuration having a catalyst-filled layer filled with a solid catalyst in the inside, wherein a liquid (in the reducing, e.g., the raw material liquid) and a gas (in the reducing, hydrogen) flow together from above the reactor to the catalyst-filled layer in a downward flow (gas-liquid downward cocurrent flow).

The FIGURE is a flow diagram illustrating an example of the reducing in the production method according to an embodiment of the present invention in the case of using a trickle-bed reactor. The FIGURE, reference numeral 1 denotes a reactor (trickle-bed reactor), reference numeral 2 denotes a supply line for the raw material liquid, and reference numeral 3 denotes a supply line for hydrogen. In addition, reference numeral 4 denotes a reaction mixture release line, reference numeral 5 denotes a high-pressure gas-liquid separator, and reference numeral 6 denotes a hydrogen recycle line. Hereinafter, the production method according to an embodiment of the present invention using a trickle-bed reactor is briefly described with reference to the FIGURE.

First, the raw material liquid and hydrogen are continuously supplied from above the trickle-bed reactor 1, and then inside the reactor, 3,4-dihydroxytetrahydrofuran and hydrogen in the raw material liquid are allowed to react in the presence of a catalyst (a catalyst for reduction reaction according to an embodiment of the present invention) in the catalyst-filled layer to produce a reduced product (a reaction product). Then, a reaction mixture containing the reduced product is continuously taken out from the reaction mixture release line 4 below the trickle-bed reactor 1, then hydrogen is separated from the reaction mixture with the high-pressure gas-liquid separator 5 as necessary, and then the reduced product is purified and isolated in purifying. In addition, hydrogen separated with the high-pressure gas-liquid separator 5 can be supplied through the hydrogen recycle line 6 to the trickle-bed reactor 1, thereby enabling the reuse thereof in the reaction.

Employment of a trickle-bed reactor as a reactor allows the reaction to proceed in a gas-liquid-solid three-phase system without vaporizing the raw material 3,4-dihydroxytetrahydrofuran, and thus is advantageous from the viewpoint of cost. In addition, the raw material liquid containing 3,4-dihydroxytetrahydrofuran flows downward while forming a thin film on the catalyst surface in the trickle-bed reactor, and thus the distance from the interface between the raw material liquid and hydrogen (gas-liquid interface) to the catalyst surface is short. This facilitates the diffusion of hydrogen dissolved in the raw material liquid to the catalyst surface, enabling efficient production of a particular reduced product. Furthermore, the process of separating the catalyst from the reaction product of 3,4-dihydroxytetrahydrofuran and hydrogen is also unnecessary, and a catalyst regeneration procedure is also easy. Thus, the production process is simple and excellent from the viewpoint of cost.

Here, the material, shape, size, and the like (e.g., such as column diameter and column height) of the trickle-bed reactor are not particularly limited, and the trickle-bed reactor can be appropriately selected according to the scale of the reaction and the like from among well-known or commonly used trickle-bed reactors. In addition, the trickle-bed reactor may be a reactor constituted of a single reaction tube, or may be a multi-stage reactor constituted of a plurality of reaction tubes. The number of reaction tubes in the case where the trickle-bed reactor is a multi-stage reactor can be appropriately selected, and is not particularly limited. Moreover, in the case where the trickle-bed reactor is a multi-stage reactor, the reactor may have a plurality of reaction tubes provided in series, or a plurality of reaction tubes arranged in parallel.

Furthermore, the catalyst-filled layer inside the trickle-bed reactor may, as necessary, be divided (separated) and placed in two or more positions, for example, to prevent overheating due to heat of reaction.

The production method according to an embodiment of the present invention may include an additional process as necessary, in addition to the reducing. Examples of the additional process include preparing and purifying the raw material liquid before supplying the raw material liquid and hydrogen to the reactor; and separating and purifying a reaction mixture (e.g., a mixture of products, such as 3,4-dihydroxytetrahydrofuran, hydrogen, and a reduced product) discharged (flown out) from the reactor. Here, these processes may be carried out in a line separate from that for the reducing, or may be carried out in a series (in-line) with the reducing.

The production method according to an embodiment of the present invention may include, for example, producing 3,4-dihydroxytetrahydrofuran, the raw material in the reducing, prior to the reducing. For example, the producing 3,4-dihydroxytetrahydrofuran preferably includes producing 3,4-dihydroxytetrahydrofuran (in particular, 1,4-anhydroerythritol) particularly by an intramolecular dehydration reaction (intramolecular cyclodehydration reaction) of erythritol (it may be referred to as the "dehydration reaction").

Dehydration Reaction

The intramolecular dehydration reaction of erythritol in the dehydration reaction can be carried out by a well-known method and is not particularly limited, but the reaction can be allowed to proceed, for example, by heating erythritol in the presence of an acid catalyst. Here, the dehydration reaction may be carried out in a line separate from that for the reducing, or may be carried out in a series with the reducing.

Erythritol used as a raw material in the dehydration reaction is not particularly limited and may be erythritol produced by chemical synthesis or may be erythritol derived from saccharides, such as glucose, by fermentation technology. Among them, from the viewpoint of reducing the load on the environment, erythritol derived from saccharides, such as glucose, by fermentation technology is preferably used. In addition, erythritol (unreacted erythritol) recovered from a reaction mixture obtained by the dehydration reaction can be reused.

A well-known or commonly used acid can be used as the acid catalyst used in the dehydration reaction, and the acid is not particularly limited. Examples thereof include inorganic acids, such as hydrochloric acid, sulfuric acid, nitric acid, phosphoric acid, polyphosphoric acid, metaphosphoric acid, condensed phosphoric acid, hydrobromic acid, perchloric acid, hypochlorous acid and chlorous acid; organic acids, such as p-toluenesulfonic acid, trichloroacetic acid, trifluoroacetic acid, and trifluoromethanesulfonic acid; and solid acids, such as cation exchange resins, zeolites, silica-alumina, and heteropolyacids (such as phosphomolybdic acid). Among them, solid acids are preferred from the viewpoint of ease of separation from products and the like, and ease of regeneration treatment. Here, commercially available products can be used as the acid catalyst, and, for example, exemplified by commercially available solid acids under trade name "Amberlyst" (available from Dow Chemical Co., Ltd.) and trade name "Nafion" (available from Du Pont Co., Ltd.). Here, one type of the acid (acid catalyst) can be used alone, or two or more types thereof can be used in combination.

The reaction (intramolecular dehydration reaction) can be allowed to proceed in the absence of a solvent and can be allowed to proceed in the presence of a solvent. Examples of the solvent include water; alcohols, such as methanol, ethanol, isopropanol, and n-butanol; ethers, such as 1,4-dioxane; and highly polar organic solvents, such as dimethyl sulfoxide (DMSO), dimethylformamide (DMF), and dimethylacetamide (DMAc). Among them, from the viewpoint of excellent reactivity, and ease of handling and disposal, at least water is preferably contained as a solvent. Here, one type of the solvent can be used alone, or two or more types thereof can be used in combination.

The reaction temperatures (heating temperatures) of the reaction (intramolecular dehydration reaction) is not particularly limited, but is preferably from 40 to 240° C., more preferably from 80 to 200° C., and still more preferably from 120 to 180° C. Controlling the reaction temperature within the above range can facilitate the intramolecular dehydration reaction of erythritol more efficiently. Here, the reaction temperature may be controlled to be constant (substantially constant) in the reaction or may be controlled to change stepwise or continuously.

The time (reaction time) of the reaction (intramolecular dehydration reaction) is not particularly limited, but is preferably from 1 to 100 hours, more preferably from 2 to 50 hours, and still more preferably from 3 to 30 hours. When the reaction time is less than 1 hour, the reaction rate (conversion) of erythritol may not sufficiently increase. On the other hand, the reaction time exceeding 100 hours may be disadvantageous from the viewpoint of cost.

The reaction (intramolecular dehydration reaction) can be carried out in any atmosphere; such as in an air atmosphere and in an inert gas atmosphere, such as nitrogen or argon. In particular, from the viewpoint of improving the selectivity of 3,4-dihydroxytetrahydrofuran, the reaction is preferably carried out in an inert gas atmosphere. In addition, the reaction (intramolecular dehydration reaction) can be carried out under any of normal pressure, increased pressure, and reduced pressure. In particular, from the viewpoint of improving the conversion of erythritol, the reaction is preferably carried out under increased pressure. For example, in the case where water is used as a solvent, the reaction temperature can be increased to 100° C. or higher by carrying out the reaction under increased pressure, and thus the conversion of erythritol can be efficiently increased.

The reaction (intramolecular dehydration reaction) can be carried in any format, such as a batch format, a semi-batch format, and a continuous flow format.

The dehydration reaction produces 3,4-dihydroxytetrahydrofuran. 3,4-dihydroxytetrahydrofuran thus obtained is then used as a raw material in the reducing, but it can be used after being isolated from the reaction mixture obtained by the dehydration reaction by a well-known or commonly used method (e.g., such as distillation, adsorption, ion exchange, crystallization, and extraction), or may be used without being isolated from the reaction mixture (as necessary, after removing the acid catalyst or the like).

EXAMPLES

Hereinafter, the present invention is more specifically described by examples, but the present invention is not limited by these examples.

Production Example of Metal Catalyst (1)

Production Example 1

Production of Catalyst (ReOx-Au/CeO$_2$)

In 250 mL of distilled water at 20° C., 0.027 g of hydrogen tetrachloroaurate (III) tetrahydrate (HAuCl$_4$.4H$_2$O available from Wako Pure Chemical Industries, Ltd.) was dissolved to prepare a tetrachloroaurate (III) aqueous solution. The tetrachloroaurate (III) aqueous solution was heated to 80° C., and then 3.947 g of cerium oxide (trade designation "HS", available from Daiichi Kigenso Kagaku Kogyo Co., Ltd.) was added. Then 0.1 M ammonia aqueous solution was added until the pH of the suspended tetrachloroaurate (III) aqueous solution reached 8 and stirred for 4 hours to precipitate out gold hydroxide. Thereafter, cerium oxide supporting gold hydroxide was recovered by suction filtration. The mixture was dried overnight in a dryer at 110° C., then the temperature was increased at a rate of 1° C./min in an air atmosphere, and calcined at 400° C. for 4 hours to obtain cerium oxide supporting gold [Au/CeO$_2$].

On the other hand, 0.052 g of ammonium perrhenate (NH$_4$ReO$_4$, available from Sigma-Aldrich Co. LLC) was dissolved in 10 mL of distilled water at 20° C. to prepare an ammonium perrhenate aqueous solution. Then, to 3.564 g of [Au/CeO$_2$] obtained above, a total amount of the ammonium perrhenate aqueous solution was added in five portions while preventing liquid pooling, heated at 80° C. and stirred to impregnate, and then this was dried overnight in a dryer at 110° C. Thereafter, the temperature was increased at a rate of 1° C./min, and the mixture was calcined at 400° C. for 4 hours to obtain a catalyst (ReOx-Au/CeO$_2$) supporting rhenium in an amount of 1 wt. % and [Au/Re]=0.3. Here, the valency of Re in the catalyst (ReOx-Au/CeO$_2$) is not constant or unstable, and thus is described as "ReO$_x$". The same applies to the catalysts below. Here, the catalyst prepared in Production Example 1 also corresponds to the catalyst (A).

Production Example of Metal Catalyst (2)

Production Example 2

Production of Catalyst (ReOx/Norit Rx3 EXTRA)

In 15 mL of distilled water at 80° C., 0.0639 g of ammonium perrhenate (NH$_4$ReO$_4$, available from Sigma-Aldrich Co. LLC) was dissolved to prepare an ammonium perrhenate aqueous solution. Then, to 1.4673 g of an activated carbon (trade name "Norit Rx3 EXTRA", available from CABOT Corporation), a total amount of the ammonium perrhenate aqueous solution was added in five portions while preventing liquid pooling, heated at 80° C. and stirred to impregnate. The mixture was dried overnight in a dryer at 110° C. to obtain a catalyst (ReOx/Norit Rx3 EXTRA). Rhenium was supported in an amount of 3 wt %. Here, the catalyst prepared in Production Example 2 also corresponds to the catalyst (B).

Production Example 3

Production of Catalyst (ReOx/Norit Rx3 EXTRA)

A catalyst (ReOx/Norit Rx3 EXTRA) was produced in the same manner as in Production Example 2 except for changing the amount of ammonium perrhenate to support rhenium in an amount of 6 wt. %. Here, the catalyst prepared in Production Example 3 also corresponds to the catalyst (B).

Production Example 4

Production of Catalyst (ReOx/BP2000)

A catalyst (ReOx/BP2000) was produced in the same manner as in Production Example 3 except for using an activated carbon of trade designation "BP2000" (carbon black, available from CABOT Corporation). Here, the catalyst prepared in Production Example 4 also corresponds to the catalyst (B).

Production Example 5

Production of Catalyst (ReOx/VXC72)

A catalyst (ReOx/VXC72) was produced in the same manner as in Production Example 3 except for using trade name "Vulcan XC72" (carbon black, available from CABOT Corporation) as the activated carbon. Here, the catalyst prepared in Production Example 5 also corresponds to the catalyst (B).

Production Example 6

Production of Catalyst (ReOx/VXC72R)

A catalyst (ReOx/VXC72R) was produced in the same manner as in Production Example 3 except for using trade name "Vulcan XC72R" (carbon black, available from CABOT Corporation) as the activated carbon. Here, the catalyst prepared in Production Example 6 also corresponds to the catalyst (B).

Production Example 7

Production of Catalyst (ReOx/Shirasagi FAC-10)

A catalyst (ReOx/Shirasagi FAC-10) was produced in the same manner as in Production Example 3 except for using trade name "Shirasagi FAC-10" (available from Osaka Gas Chemicals Co., Ltd.) as the activated carbon. Here, the catalyst prepared in Production Example 7 also corresponds to the catalyst (B).

Production Example 8

Production of Catalyst (ReOx/Shirasagi M)

A catalyst (ReOx/Shirasagi M) was produced in the same manner as in Production Example 3 except for using trade name "Shirasagi M" (available from Osaka Gas Chemicals Co., Ltd.) as the activated carbon. Here, the catalyst prepared in Production Example 8 also corresponds to the catalyst (B).

Production Example 9

Production of Catalyst (ReOx/TiO$_2$)

A catalyst (ReOx/TiO$_2$) was produced in the same manner as in Production Example 3 except for using titania (trade name "P25", available from Nippon Aerosil Co., Ltd.)

instead of the activated carbon. Here, the catalyst prepared in Production Example 9 also corresponds to the catalyst (A).

Production Example 10

Production of Catalyst (ReOx/Al$_2$O$_3$)

A catalyst (ReOx/Al$_2$O$_3$) was produced in the same manner as in Production Example 3 except for using alumina (prepared by calcining boehmite available from Wako Pure Chemical Industries, Ltd. at 600° C. for 3 hours) instead of the activated carbon. Here, the catalyst prepared in Production Example 10 also corresponds to the catalyst (A).

Production Example 11

Production of Catalyst (ReOx/ZrO$_2$)

A catalyst (ReOx/ZrO$_2$) was produced in the same manner as in Production Example 3 except for using zirconia (trade name "RC-100P", available from Daiichi Kigenso Kagaku Kogyo Co., Ltd.) instead of the activated carbon. Here, the catalyst prepared in Production Example 11 also corresponds to the catalyst (A).

Production Example 12

Production of Catalyst (ReOx/SiO$_2$)

A catalyst (ReOx/SiO$_2$) was produced in the same manner as in Production Example 3 except for using silica (trade name "G-6", available from Fuji Silicia Chemical, Co., Ltd.) instead of the activated carbon. Here, the catalyst prepared in Production Example 12 also corresponds to the catalyst (A).

Production Example 13

Production of Catalyst (ReOx/HZ SM-5)

A catalyst (ReOx/HZSM-5) was produced in the same manner as in Production Example 3 except for using zeolite (trade name "HZSM-5", available from Süd-Chemie) instead of the activated carbon. Here, the catalyst prepared in Production Example 13 also corresponds to the catalyst (A).

Production Example 14

Production of Catalyst (ReOx/HBEA)

A catalyst (ReOx/HBEA) was produced in the same manner as in Production Example 3 except for using zeolite (trade name "HBEA", available from Tosoh Corporation) instead of the activated carbon. Here, the catalyst prepared in Production Example 14 also corresponds to the catalyst (A).

Production Example 15

Production of Catalyst (ReOx/HUSY)

A catalyst (ReOx/HUSY) was produced in the same manner as in Production Example 3 except for using zeolite (trade name "HUSY", available from Tosoh Corporation) instead of the activated carbon. Here, the catalyst prepared in Production Example 15 also corresponds to the catalyst (A).

Production Example 16

Production of Catalyst (ReOx/Char Carbon)

A catalyst (ReOx/Char Carbon) was produced in the same manner as in Production Example 3 except for using trade name "Char Carbon" (charcoal, available from Wako Pure Chemical Industries, Ltd.) as the activated carbon. Here, the catalyst prepared in Production Example 16 also corresponds to the catalyst (B).

Production Example 17

Production of Catalyst (MoOx/Norit Rx3 EXTRA)

A catalyst (MoOx/Norit Rx3 EXTRA) was produced in the same manner as in Production Example 3 except for using ammonium molybdate (available from Wako Pure Chemical Industries, Ltd.) instead of ammonium perrhenate. Here, the catalyst prepared in Production Example 17 also corresponds to the catalyst (B).

Production Example 18

Production of Catalyst (WOx/Norit Rx3 EXTRA)

A catalyst (WOx/Norit Rx3 EXTRA) was produced in the same manner as in Production Example 3 except for using ammonium tungstate (available from Strem Chemicals Inc.) instead of ammonium perrhenate. Here, the catalyst prepared in Production Example 18 also corresponds to the catalyst (B).

Reference Example 1

Production of 3,4-dihydroxytetrahydrofuran

Into an autoclave, 1 g of erythritol, 4 g of water, and 0.15 g of "Amberlyst 70" (trade designation, available from Dow Chemical Co., Ltd.) as a catalyst were charged, and a reaction was performed in an argon atmosphere at a pressure of 5 MPa and a temperature of 160° C. for 24 hours to obtain 3,4-dihydroxytetrahydrofuran. The conversion of erythritol was 98.6%, the selectivity of 3,4-dihydroxytetrahydrofuran was 97.2%, and the yield was 95.8%.

Examples 1 to 6

Reduction of 3,4-dihydroxytetrahydrofuran

In a glass autoclave inner cylinder, a stirrer chip, 150 mg of the catalyst (ReOx-Au/CeO$_2$) obtained in Production Example 1, the catalyst (ReOx/Norit Rx3 EXTRA) obtained in Production Example 2 in an amount shown in Table 1, 4 g of 1,4-dioxane, and 0.5 g of 3,4-dihydroxytetrahydrofuran were placed. The autoclave inner cylinder was placed in a 190-mL autoclave (high-pressure batch reactor) and the lid was closed. Next, an operation of filling the inside of the autoclave with 1 MPa hydrogen and then evacuating the hydrogen was repeated three times to expel inside air from the autoclave. The autoclave was charged with hydrogen to exhibit 5.5 MPa at room temperature, thereby exhibiting 8 MPa at 140° C. (hydrogen pressure: 8 MPa).

Next, the autoclave was set in a heating device with a magnetic stirrer and heated to increase the temperature inside the reactor (inside the autoclave) to 140° C., and stirred for 24 hours (reaction time=24 hours) while maintaining the reaction temperature at 140° C. Thereafter, the inside of the reactor was cooled to room temperature, and the hydrogen inside the autoclave was released to depressurize the inside of the autoclave.

The solution after the reaction was analyzed by FID analysis and GC-MS using gas chromatography (gas chromatograph instrument: "GC-2014" (available from Shimadzu Corporation), GC column: TC-WAX, DB-FFAP, detector: FID). The conversion of 3,4-dihydroxytetrahydrofuran and the selectivity of the product were calculated therefrom. The analytical results are shown in Table 1.

TABLE 1

|  | Mass of catalyst 2 (mg) | Conv./% | Selectivity/% | | | |
|---|---|---|---|---|---|---|
|  |  |  | 1,4-BuD | THF | γ-Bul | 1-BuOH |
| Example 1 | 50 | 95.0 | 56.1 | 12.1 | 4.3 | 1.9 |
| Example 2 | 100 | 95.3 | 68.9 | 13.2 | 3.2 | 2.6 |
| Example 3 | 150 | 98.1 | 73.8 | 16.9 | 2.2 | 3.5 |
| Example 4 | 200 | 98.7 | 77.3 | 15.0 | 1.8 | 3.4 |
| Example 5 | 250 | 98.9 | 76.5 | 16.5 | 1.2 | 4.0 |
| Example 6 | 300 | 99.2 | 76.8 | 16.4 | 1.2 | 3.9 |

Examples 7 and 8

A reduction reaction of 3,4-dihydroxytetrahydrofuran was performed in the same manner as in Example 4 except for changing the reaction temperature as shown in Table 2. The analytical results are shown in Table 2.

TABLE 2

|  | Temperature/K | Conv./% | Selectivity/% | | | |
|---|---|---|---|---|---|---|
|  |  |  | 1,4-BuD | THF | γ-Bul | 1-BuOH |
| Example 7 | 393 | 41.0 | 57.9 | 12.6 | 0.9 | 2.6 |
| Example 4 | 413 | 98.7 | 77.3 | 15.0 | 1.8 | 3.4 |
| Example 8 | 433 | 99.9 | 67.6 | 23.5 | 3.1 | 3.4 |

Examples 9 to 12

A reduction reaction of 3,4-dihydroxytetrahydrofuran was performed in the same manner as in Example 4 except for changing the hydrogen partial pressure as shown in Table 3. The analytical results are shown in Table 3.

TABLE 3

|  | Pressure/MPa | Conv./% | Selectivity/% | | | |
|---|---|---|---|---|---|---|
|  |  |  | 1,4-BuD | THF | γ-Bul | 1-BuOH |
| Example 9 | 2 | 69.2 | 45.6 | 6.9 | 8.1 | 1.6 |
| Example 10 | 4 | 91.0 | 68.7 | 10.4 | 5.5 | 2.3 |
| Example 11 | 6 | 94.7 | 76.0 | 12.5 | 3.6 | 3.0 |
| Example 4 | 8 | 98.7 | 77.3 | 15.0 | 1.8 | 3.4 |
| Example 12 | 10 | 98.9 | 75.3 | 18.3 | 0.7 | 4.0 |

Examples 13 to 28 and Comparative Example 1

A reduction reaction of 3,4-dihydroxytetrahydrofuran was performed in the same manner as in Example 2 except for changing the metal catalyst (2) used as shown in Table 4 or not using the metal catalyst (2). The analytical results are shown in Table 4.

TABLE 4

|  | Catalyst 2 |  | Conv./% | Selectivity/% | | | |
|---|---|---|---|---|---|---|---|
|  |  |  |  | 1,4-BuD | THF | γ-Bul | 1-BuOH |
| Example 13 | ReO$_x$/TiO$_2$ | Production Example 9 | >99.9 | 24.1 | 49.1 | 0.0 | 17.0 |
| Example 14 | ReO$_x$/Al$_2$O$_3$ | Production Example 10 | >99.9 | 23.7 | 43.7 | 0.0 | 14.9 |
| Example 15 | ReO$_x$/ZrO$_2$ | Production Example 11 | >99.9 | 4.9 | 60.4 | 0.0 | 29.2 |
| Example 16 | ReO$_x$/SiO$_2$ | Production Example 12 | 55.2 | 19.2 | 40.6 | 0.8 | 6.3 |
| Example 17 | ReO$_x$/BP2000 | Production Example 4 | >99.9 | 68.7 | 22.0 | 0.3 | 7.1 |
| Example 18 | ReO$_x$/VXC72 | Production Example 5 | >99.9 | 62.3 | 22.8 | 2.5 | 4.4 |
| Example 19 | ReO$_x$/VXC72R | Production Example 6 | >99.9 | 61.1 | 25.3 | 1.7 | 5.2 |
| Example 20 | ReO$_x$/Shirasagi FAC-10 | Production Example 7 | >99.9 | 61.8 | 23.0 | 3.3 | 3.6 |
| Example 21 | ReO$_x$/Shirasagi M | Production Example 8 | >99.9 | 60.7 | 21.1 | 3.6 | 3.9 |
| Example 22 | ReO$_x$/Norit Rx3 EXTRA | Production Example 3 | >99.9 | 71.6 | 17.7 | 2.1 | 3.7 |
| Example 23 | ReO$_x$/HZSM-5 | Production Example 13 | 80.8 | 0.6 | 86.4 | 1.8 | 5.3 |
| Example 24 | ReO$_x$/HBEA | Production Example 14 | 61.4 | 0.2 | 83.6 | 1.2 | 5.6 |
| Example 25 | ReO$_x$/HUSY | Production Example 15 | 57.5 | 5.3 | 74.4 | 1.4 | 5.9 |
| Example 26 | ReO$_x$/Char Carbon | Production Example 16 | >99.9 | 63.3 | 20.3 | 3.6 | 3.1 |
| Example 27 | MoO$_x$/Norit Rx3 EXTRA | Production Example 17 | 4.9 | 0.0 | 3.9 | 4.7 | 0.0 |
| Example 28 | WO$_x$/Norit Rx3 EXTRA | Production Example 18 | 17.6 | 0.0 | 4.7 | 2.5 | 0.0 |

TABLE 4-continued

| | Catalyst 2 | Conv./% | Selectivity/% | | | |
| | | | 1,4-BuD | THF | γ-Bul | 1-BuOH |
|---|---|---|---|---|---|---|
| Comparative Example 1 | — | — | >99.9 | 1.6 | 2.5 | 0.0 | 0.1 |

As shown in Table 4, in the case where a catalyst in which rhenium was supported on an activated carbon was used as the metal catalyst (2) (Examples 17 to 22 and 26), 1,4-butanediol was obtained with high selectivity and high yield relative to the comparative example. In the case where a catalyst in which rhenium, molybdenum, or tungsten was supported on an inorganic oxide was used as the metal catalyst (2) (Examples 13 to 16, 23 to 25, 27, and 28), tetrahydrofuran was obtained with high selectivity relative to the comparative example. Among them, in the case where a catalyst in which rhenium was supported on titania, alumina, or zirconia was used as the metal catalyst (2) (Examples 13 to 15), the conversion of 3,4-dihydroxytetrahydrofuran was even higher.

Production Example of Catalyst (A)

Production Example 19

Production of Catalyst (ReOx/CeO$_2$)

In 15 mL of distilled water at 80° C., 0.144 g of ammonium perrhenate (NH$_4$ReO$_4$, available from Sigma-Aldrich Co. LLC) was dissolved to prepare an ammonium perrhenate aqueous solution. Then, to 10.0 g of trade name "HS" (cerium oxide, available from Daiichi Kigenso Kagaku Kogyo Co., Ltd.), a total amount of the ammonium perrhenate aqueous solution was added in five portions while preventing liquid pooling, heated at 80° C. and stirred to impregnate. The mixture was dried overnight in a dryer at 110° C. to obtain a catalyst (ReOx/CeO$_2$). Rhenium was supported in an amount of 1 wt %. In addition, the catalyst prepared in Production Example 19 also corresponds to the metal catalyst (2).

Production Example 20

Production of Catalyst (CeO$_2$)

Trade name "HS" (cerium oxide, available from Daiichi Kigenso Kagaku Kogyo Co., Ltd.) was used as a catalyst (CeO$_2$).

Production Example of Catalyst (B)

Production Example 21

Production of Catalyst (BP2000)

Trade name "BP2000" (carbon black, available from CABOT Corporation) was used as a catalyst (BP2000).

Production Example 22

Production of Catalyst (ReOx/BP2000)

A catalyst (ReOx/BP2000) was produced in the same manner as in Production Example 4 except for changing the amount of ammonium perrhenate to support rhenium in an amount of 1 wt. %. Here, the catalyst prepared in Production Example 22 also corresponds to the metal catalyst (2).

Production Example 23

Production of Catalyst (ReOx/BP2000)

A catalyst (ReOx/BP2000) was produced in the same manner as in Production Example 4 except for changing the amount of ammonium perrhenate to support rhenium in an amount of 3 wt. %. Here, the catalyst prepared in Production Example 23 also corresponds to the metal catalyst (2).

Production Example 24

Production of Catalyst (ReOx/BP2000)

A catalyst (ReOx/BP2000) was produced in the same manner as in Production Example 4 except for changing the amount of ammonium perrhenate to support rhenium in an amount of 9 wt. %. Here, the catalyst prepared in Production Example 24 also corresponds to the metal catalyst (2).

Examples 29 to 38 and Comparative Examples 2 to 6

Reduction of 3,4-dihydroxytetrahydrofuran

In a glass autoclave inner cylinder, a stirrer chip, 150 mg of the catalyst (A) and 150 mg of the catalyst (B) obtained in each production example shown in Table 5 (however, "-" indicates no addition), 4 g of 1,4-dioxane, and 0.5 g of 3,4-dihydroxytetrahydrofuran were placed. The autoclave inner cylinder was placed in a 190-mL autoclave (high-pressure batch reactor) and the lid was closed. Next, an operation of filling the inside of the autoclave with 1 MPa hydrogen and then evacuating the hydrogen was repeated three times to expel inside air from the autoclave. The autoclave was charged with hydrogen to exhibit 5.5 MPa at room temperature, thereby exhibiting 8 MPa at 140° C. (hydrogen pressure: 8 MPa).

Next, the autoclave was set in a heating device with a magnetic stirrer and heated to increase the temperature inside the reactor (inside the autoclave) to 140° C., and stirred for 24 hours (reaction time=24 hours) while maintaining the reaction temperature at 140° C. Thereafter, the inside of the reactor was cooled to room temperature, and the hydrogen inside the autoclave was released to depressurize the inside of the autoclave.

The solution after the reaction was analyzed by FID analysis and GC-MS using gas chromatography (gas chromatograph instrument: "GC-2014" (available from Shimadzu Corporation), GC column: TC-WAX, DB-FFAP, detector: FID). The conversion of 3,4-dihydroxytetrahydrofuran and the selectivity of the product were calculated therefrom. The analytical results are shown in Table 5.

TABLE 5

| | Catalyst A | | Catalyst B | | Conv./% | Selectivity/% | | | |
|---|---|---|---|---|---|---|---|---|---|
| | | | | | | 1,4-BuD | THF | γ-Bul | 1-BuOH |
| Comparative Example 2 | ReO$_X$—Au/CeO$_2$ | Production Example 1 | — | — | 64.1 | 0.4 | 0.9 | 0.4 | 0.0 |
| Example 29 | ReO$_X$—Au/CeO$_2$ | Production Example 1 | BP2000 | Production Example 21 | 25.0 | 69.2 | 2.2 | 1.2 | 0.3 |
| Example 30 | ReO$_X$—Au/CeO$_2$ | Production Example 1 | ReO$_X$/BP2000 (Re = 1%) | Production Example 22 | 76.4 | 69.5 | 8.8 | 3.1 | 2.6 |
| Example 31 | ReO$_X$—Au/CeO$_2$ | Production Example 1 | ReO$_X$/BP2000 (Re = 3%) | Production Example 23 | >99.9 | 85.3 | 7.8 | 1.9 | 1.8 |
| Example 32 | ReO$_X$—Au/CeO$_2$ | Production Example 1 | ReO$_X$/BP2000 (Re = 6%) | Production Example 4 | >99.9 | 82.4 | 12.6 | 0.5 | 2.5 |
| Example 33 | ReO$_X$—Au/CeO$_2$ | Production Example 1 | ReO$_X$/BP2000 (Re = 9%) | Production Example 24 | 98.6 | 76.0 | 18.2 | 0.6 | 2.8 |
| Comparative Example 3 | ReO$_X$/CeO$_2$ | Production Example 19 | — | — | 3.6 | 0.9 | 40.9 | 7.5 | 0.0 |
| Example 34 | ReO$_X$/CeO$_2$ | Production Example 19 | BP2000 | Production Example 21 | 24.0 | 71.1 | 2.3 | 1.5 | 0.4 |
| Example 35 | ReO$_X$/CeO$_2$ | Production Example 19 | ReO$_X$/BP2000 (Re = 1%) | Production Example 22 | 73.0 | 87.7 | 5.0 | 1.0 | 0.6 |
| Example 36 | ReO$_X$/CeO$_2$ | Production Example 19 | ReO$_X$/BP2000 (Re = 3%) | Production Example 23 | 96.8 | 86.2 | 7.4 | 1.5 | 2.0 |
| Example 37 | ReO$_X$/CeO$_2$ | Production Example 19 | ReO$_X$/BP2000 (Re = 9%) | Production Example 24 | 87.2 | 79.7 | 5.8 | 2.3 | 2.5 |
| Comparative Example 4 | CeO$_2$ | Production Example 20 | — | — | 3.2 | 0.0 | 0.0 | 7.2 | 0.0 |
| Example 38 | CeO$_2$ | Production Example 20 | ReO$_X$/BP2000 (Re = 3%) | Production Example 23 | 84.9 | 89.6 | 4.4 | 1.2 | 1.0 |
| Comparative Example 5 | — | — | BP2000 | Production Example 21 | 1.6 | 0.0 | 0.0 | 14.8 | 0.0 |
| Comparative Example 6 | — | — | ReO$_X$/BP2000 (Re = 3%) | Production Example 23 | 3.3 | 18.4 | 15.7 | 4.5 | 4.2 |

As shown in Table 5, in the case where an activated carbon on which no rhenium was supported was used as the catalyst (B) (Example 29 and Example 34), the conversion of 3,4-dihydroxytetrahydrofuran was high, and the selectivity of 1,4-butanediol was high, compared to the case of not using the catalyst (B) (Comparative Examples 2 to 4). In addition, in the case where an activated carbon on which rhenium was supported was used as the catalyst (B) (Examples 30 to 33 and Examples 35 to 38), the conversion of 3,4-dihydroxytetrahydrofuran and the selectivity of 1,4-butanediol were even higher. In addition, in the case where a catalyst in which gold and rhenium were supported (Examples 29 to 33), a catalyst in which only rhenium was supported (Examples 34 to 37), and a catalyst in which neither gold nor rhenium was supported (Example 38) were used as the catalyst (A), the conversion of 3,4-dihydroxytetrahydrofuran and the selectivity of 1,4-butanediol were equivalent. Furthermore, in the case where the catalyst (A) was not used (Comparative Examples 5 and 6), the conversion of 3,4-dihydroxytetrahydrofuran was extremely low.

Abbreviations in the table indicate the following compounds.

1,4-BuD: 1,4-butanediol
THF: tetrahydrofuran
γ-Bul: γ-butyrolactone
1-BuOH: 1-butanol
Conv.: conversion Here, in the examples, the conversion was calculated by Formula (1) below, and the selectivity was calculated by Formula (2) below.

Conversion (%)={amount (mol) of 2,3-dihydroxytetrahydrofuran used as raw material—amount (mol) of remaining 2,3-dihydroxytetrahydrofuran}/amount (mol) of 2,3-dihydroxytetrahydrofuran used as raw material×100    (1)

Selectivity (%) of substance A=amount (mol) of substance A produced/{amount (mol) of 2,3-dihydroxytetrahydrofuran used as raw material–amount (mol) of remaining 2,3-dihydroxytetrahydrofuran}×100    (2)

INDUSTRIAL APPLICABILITY

The catalyst for reduction reaction according to the present invention can be used in a reduction reaction with hydrogen using 3,4-dihydroxytetrahydrofuran as a raw material.

REFERENCE SIGNS LIST

1 Trickle-bed reactor
2 Raw material liquid supply line
3 Hydrogen supply line
4 Reaction mixture release line
5 High-pressure gas-liquid separator
6 Hydrogen recycle line

The invention claimed is:

1. A catalyst for reduction reaction of 3,4-dihydroxytetrahydrofuran, the catalyst being used in a reaction for reducing 3,4-dihydroxytetrahydrofuran by reaction with hydrogen, wherein the catalyst contains a metal catalyst (1) and a metal catalyst (2) below;
   metal catalyst (1): a catalyst containing M1 and M2 below as metal species and supported on a carrier; and
   metal catalyst (2): a catalyst containing M1 below as a metal species and supported on a carrier;
   M1: one or more selected from the group consisting of iron and elements belonging to periods 4 to 6 and belonging to groups 5 to 7 of the periodic table; and M2: one or more selected from the group consisting of ruthenium, osmium, and elements belonging to periods 4 to 6 and belonging to groups 9 to 11 of the periodic table.

2. The catalyst for reduction reaction of 3,4-dihydroxytetrahydrofuran according to claim 1, wherein the M1 in the metal catalyst (1) is rhenium and the M2 in the metal catalyst (1) is gold.

3. The catalyst for reduction reaction of 3,4-dihydroxytetrahydrofuran according to claim 1, wherein the carrier in the metal catalyst (1) is cerium oxide.

4. The catalyst for reduction reaction of 3,4-dihydroxytetrahydrofuran according to claim 1, wherein the M1 in the metal catalyst (2) is rhenium.

5. The catalyst for reduction reaction of 3,4-dihydroxytetrahydrofuran according to claim 1, wherein the carrier in the metal catalyst (2) is an activated carbon.

6. A method for producing a 3,4-dihydroxytetrahydrofuran reduced product, the method comprising reducing 3,4-dihydroxytetrahydrofuran by reaction with hydrogen, wherein the reaction of 3,4-dihydroxytetrahydrofuran and hydrogen is allowed to proceed in the presence of the catalyst for reduction reaction of 3,4-dihydroxytetrahydrofuran described in claim 1.

7. The method for producing a 3,4-dihydroxytetrahydrofuran reduced product according to claim 6, wherein the reaction of 3,4-dihydroxytetrahydrofuran and hydrogen is performed in an atmosphere with a hydrogen partial pressure of 3 MPa or higher.

8. The method for producing a 3,4-dihydroxytetrahydrofuran reduced product according to claim 6, the method comprising subjecting erythritol to cyclodehydration to obtain 3,4-dihydroxytetrahydrofuran prior to the reducing 3,4-dihydroxytetrahydrofuran.

9. A catalyst for reduction reaction of 3,4-dihydroxytetrahydrofuran, the catalyst being used in a reaction for reducing 3,4-dihydroxytetrahydrofuran by reaction with hydrogen, wherein the catalyst contains a catalyst (A) and a catalyst (B) below; and at least one of the catalyst (A) and the catalyst (B) are catalysts in which M1 below is supported as a metal species;
catalyst (A): an inorganic oxide; and
catalyst (B): an activated carbon;
M1: one or more selected from the group consisting of iron and elements belonging to periods 4 to 6 and belonging to groups 5 to 7 of the periodic table.

10. The catalyst for reduction reaction of 3,4-dihydroxytetrahydrofuran according to claim 9, wherein the M1 is rhenium.

11. The catalyst for reduction reaction of 3,4-dihydroxytetrahydrofuran according to claim 9, wherein the inorganic oxide in the catalyst (A) is cerium oxide.

12. The catalyst for reduction reaction of 3,4-dihydroxytetrahydrofuran according to claim 9, wherein the catalyst (B) is a catalyst in which the M1 is supported as a metal species.

13. The catalyst for reduction reaction of 3,4-dihydroxytetrahydrofuran according to claim 9, wherein the catalyst (A) and the catalyst (B) are catalysts in which the M1 is supported as a metal species.

14. A method for producing a 3,4-dihydroxytetrahydrofuran reduced product, the method comprising reducing 3,4-dihydroxytetrahydrofuran by reaction with hydrogen, wherein the reaction of 3,4-dihydroxytetrahydrofuran and hydrogen is allowed to proceed in the presence of the catalyst for reduction reaction of 3,4-dihydroxytetrahydrofuran described in claim 9.

15. A method for producing a 3,4-dihydroxytetrahydrofuran reduced product, the method comprising reducing 3,4-dihydroxytetrahydrofuran by reaction with hydrogen, wherein the reaction of 3,4-dihydroxytetrahydrofuran and hydrogen is allowed to proceed by performing a reaction in the presence of a metal catalyst (1) below in a first stage and performing a reaction in the presence of a metal catalyst (2) below in a second stage;
metal catalyst (1): a catalyst containing M1 and M2 below as metal species and supported on a carrier; and
metal catalyst (2): a catalyst containing M1 below as a metal species and supported on a carrier;
M1: one or more selected from the group consisting of iron and elements belonging to periods 4 to 6 and belonging to groups 5 to 7 of the periodic table; and
M2: one or more selected from the group consisting of ruthenium, osmium, and elements belonging to periods 4 to 6 and belonging to groups 9 to 11 of the periodic table.

16. A method for producing a 3,4-dihydroxytetrahydrofuran reduced product, the method comprising reducing 3,4-dihydroxytetrahydrofuran by reaction with hydrogen, wherein the reaction of 3,4-dihydroxytetrahydrofuran and hydrogen is allowed to proceed by performing a reaction in the presence of a catalyst (A) below in a first stage and performing a reaction in the presence of a catalyst (B) below in a second stage;
wherein at least one of the catalyst (A) and the catalyst (B) are catalysts in which M1 below is supported as a metal species;
catalyst (A): an inorganic oxide; and
catalyst (B): an activated carbon;
M1: one or more selected from the group consisting of iron and elements belonging to periods 4 to 6 and belonging to groups 5 to 7 of the periodic table.

\* \* \* \* \*